United States Patent
Costella et al.

(10) Patent No.: US 12,251,492 B2
(45) Date of Patent: Mar. 18, 2025

(54) NANOFIBER-REINFORCED HYDROGEL MEDICAL DRESSINGS

(71) Applicant: LUNA INNOVATIONS INCORPORATED, Roanoke, VA (US)

(72) Inventors: Lauren Anne Costella, Roanoke, VA (US); Christopher K. Tison, Roanoke, VA (US); Matthew Patterson, Roanoke, VA (US); Keley Broderick, Roanoke, VA (US); Lindsay Woodard, Roanoke, VA (US); Mallory Gasbarre, Roanoke, VA (US)

(73) Assignee: LUNA LABS USA, LLC, Charlottesville, VA (US)

( * ) Notice: Subject to any disclaimer, the term of this patent is extended or adjusted under 35 U.S.C. 154(b) by 1188 days.

(21) Appl. No.: 17/046,464

(22) PCT Filed: Apr. 8, 2019

(86) PCT No.: PCT/US2019/026254
§ 371 (c)(1),
(2) Date: Oct. 9, 2020

(87) PCT Pub. No.: WO2019/199630
PCT Pub. Date: Oct. 17, 2019

(65) Prior Publication Data
US 2021/0154356 A1    May 27, 2021

Related U.S. Application Data

(60) Provisional application No. 62/654,651, filed on Apr. 9, 2018.

(51) Int. Cl.
*A61L 26/00* (2006.01)

(52) U.S. Cl.
CPC ......... *A61L 26/008* (2013.01); *A61L 26/0014* (2013.01); *A61L 26/0023* (2013.01);
(Continued)

(58) Field of Classification Search
CPC ............... A61L 26/008; A61L 26/0014; A61L 26/0023; A61L 26/0028; A61L 26/0066;
(Continued)

(56) References Cited

U.S. PATENT DOCUMENTS

| 2019/0076573 A1* | 3/2019 | Yee | A61L 31/10 |
| 2019/0101669 A1 | 4/2019 | Yee et al. | |
| 2019/0247474 A1* | 8/2019 | Chen | A61K 38/4833 |

FOREIGN PATENT DOCUMENTS

| CN | 101125216 A | * | 2/2008 | |
| EP | 3539576 A1 | * | 3/2018 | A61L 27/20 |
| WO | 03/000231 | | 1/2003 | |
| WO | WO-2010120531 A2 | * | 3/2010 | A61F 2/0063 |

(Continued)

OTHER PUBLICATIONS

International Search Report for PCT/US2019/026254, mailed Jul. 17, 2019, 5 pages.
(Continued)

*Primary Examiner* — Ophelia A Hawthorne
(74) *Attorney, Agent, or Firm* — NIXON & VANDERHYE P.C.

(57) ABSTRACT

Medical dressings include a non-woven polymeric nanofiber mat embedded within a chitosan hydrogel matrix. The dressings may be obtained by electro spinning of polymeric nanofibers and thereafter incorporating a chitosan hydrogel into interstices of the mat by vacuum or positive pressure assistance. The resulting medical dressings may be optically transparent (e.g., at least about 50% up to about 95% light transmittance), flexible, and mechanically robust. The dressings may also incorporate self-adhesion promoters to allow self-adhesion to biological tissue, e.g., ocular surfaces, and/

(Continued)

or therapeutic agents which are capable of delivering therapeutics (e.g. stem cells, drugs and the like) to the tissue surface. The dressings are especially useful as ocular bandages for the treatment and repair of ocular wounds.

29 Claims, 5 Drawing Sheets

(52) U.S. Cl.
CPC ....... *A61L 26/0028* (2013.01); *A61L 26/0066* (2013.01); *A61L 26/0071* (2013.01); *A61L 26/0095* (2013.01); *A61L 2300/406* (2013.01); *A61L 2300/41* (2013.01); *A61L 2300/64* (2013.01); *A61L 2400/12* (2013.01)

(58) Field of Classification Search
CPC ............. A61L 26/0071; A61L 26/0095; A61L 2300/406; A61L 2300/41; A61L 2300/64; A61L 2400/12; A61L 26/0019; A61L 26/0033; A61L 26/0061; A61L 27/34; A61L 15/28; A61L 15/32; A61L 15/325; A61L 15/42; A61L 15/46; A61L 27/30; A61L 27/50; A61L 29/14; A61L 31/10; A61L 31/14; A61L 31/16; A61L 2300/00; A61F 13/15; A61F 13/00; A61F 13/00063; B82Y 30/00

See application file for complete search history.

(56) References Cited

FOREIGN PATENT DOCUMENTS

WO      2013/040559         3/2013
WO      WO-2017049284 A1 *  3/2017 ....... A61F 13/00012

OTHER PUBLICATIONS

Written Opinion of the ISA for PCT/US2019/026254, mailed Jul. 17, 2019,.

Wright et al., "PDLA/PLLA and PDLA/PCL nanofibers with a chitosan-based hydrogel in composite scaffolds for tissue engineered cartilage", Journal of Tissue Engineering and Regenerative Medicine, vol. 8, No. 12, Dec. 1, 2014, pp. 946-954.

Stafiej et al., "Transparency of suture able, nanofiber reinforced, alginate hydrogels for corneal wound healing", IOVS, ARVO Annual Meeting Abstract, Jun. 1, 2017, https://iovs.arvojournals.org/article.aspx?articleid=2636932 , XP055602582.

Moreno et al., "Modulating release of ranibizumab and aflibercept from thiolated chitosan-based hydrogels for potential treatment of ocular neovascularization", Expert Opinion on Drug Delivery, vol. 14, No. 8, Jul. 3, 2017, pp. 913-925, XP055602731.

Padmanabhan et al., "Chitosan Hydrogels for Regenerative Engineering", Chitin and Chitosan for Regenerative Medicine, Sep. 5, 2015, pp. 3-40, XP055602774.

Costella et al., "BIOcular™ Dressings for Corneal Repair", IOVS, ARVO Annual Meeting Abstract, May 7, 2017, XP055602620.

Costella et al., "BIOcular Dressings for Corneal Wound Healing", IOVS, Arvo Annual Meeting Abstract, Apr. 29, 2018, XP055602611.

* cited by examiner

| Nanofiber Reinforcement Chemistry | Hydrated Secchi Disk Image | Optical Properties | Handling Properties |
|---|---|---|---|
| Collagen | | Favorable transparency, both dry and hydrated. Transparency ultimately dependant on thickness and crosslinking of sample. | Dressings are very fragile, similar to amniotic membrane |
| Nylon -6 | | Favorable transparency in both dry and hydrated state. | Good handling properties; robust dressing |
| Nylon -6/5 | | Resultant dressing is opaque, even when hydrated | Very robust dressing with good handling properties. |

FIG. 4A

| | | |
|---|---|---|
| PVA | Favorable transparency | Difficult to handle. Dressing is briddle and swells signifianctly when hydrated |
| PCL | Translucent dressing with minimal transparency | Favorable handling properties; very robust |
| 15% w/v PLLA | Moderate transparency | Robust dressing; favorable handling properties |
| 12.5% w/v PLLA | Moderate transparency | Robust dressing; favorable handling properties |

FIG. 4B

NANOFIBER-REINFORCED HYDROGEL MEDICAL DRESSINGS

CROSS-REFERENCE TO RELATED APPLICATION

This application is the U.S. national phase of International Application No. PCT/US2019/026254 filed 8 Apr. 2019 which designated the U.S. and claims priority benefits from U.S. Provisional Application Ser. No. 62/654,651 filed on Apr. 9, 2019, the entire contents of each of which are expressly incorporated hereinto by reference.

GOVERNMENT RIGHTS

This invention was made with Government support under the following Government awarded contracts: Army W81XWH-14-C-0028, Army W81XWH-16-C-0010, Army W81XWH-15-C-0139, Army W81XWH-17-C-0140, Army W81XWH-15-C-0010, DHP W81XWH-16-C-0014. The Government has certain rights to the invention.

FIELD

The disclosed embodiments herein relate generally to medical dressings, e.g., surgical dressings and bandages suitable for tissue wound treatment and/or repair. According to certain embodiments, medical dressings comprised of nano-fiber reinforced chitosan hydrogel are provided that are capable of treating ocular trauma, corneal surface defects and injuries, and other related ocular complications.

BACKGROUND

The frequency of ocular injuries, particularly those attributable to combat injuries to military personnel, has increased significantly in recent years. Maintaining vision following severe ocular trauma is critical to restoring overall quality of life. The current standard of care for treating ocular surface injuries involves the application of human amniotic membrane to the injured site. While extremely effective at stimulating repair, the required processing prior to application is time consuming and expensive, making the application of the membrane difficult in military field hospitals and other emergency situations. More severe injuries in which globe integrity has been compromised necessitate the application of preserved scleral tissue or TutoPlast® bandages, which lack the flexibility and transparency that would be beneficial for these ocular applications. Finally, there exists a need for sustained delivery of therapeutics to the corneal surface for the treatment of corneal ulcers, glaucoma, or for recovery from standard ocular surgical procedures. There is thus a definitive need for synthetic biomaterials capable of serving as bandages that may be employed in a variety of surgical procedures to treat and/or repair e.g., circulatory anastomoses, abrasions, ulcers or ocular injuries such as severe open-globe injuries. It is towards supplying such needs that the embodiments disclosed herein are directed.

SUMMARY

Generally, the embodiments disclosed herein are directed toward medical dressings or bandages comprised of a nonwoven polymeric nanofiber mat and a chitosan hydrogel impregnated throughout the thickness of the mat. The nanofiber mat is therefore embedded within the chitosan hydrogel matrix. According to certain embodiments the chitosan hydrogel will be present in a mass ratio of the nanofibers to chitosan hydrogel of 0.01:1 to 10:1, preferably 0.1:1 to 1:1. The chitosan may have a weight average molecular weight (Mw) of between about 50,000 to about 370,000 g/mol.

In certain embodiments, e.g., when used as an ocular dressing, the dressing will additionally include a surface adhesive functionality and/or a therapeutic agent. Exemplary therapeutic agents may be human stem cells or a therapeutic drug, e.g., antibiotics (such as gentamycin or fluoroquinolone compounds), non-steroidal or steroidal anti-inflammatories (such as prednisolone) and mixtures thereof. Specific therapeutic drugs include, by way of example, Ciloxan®, Vigamox®, Oculflox® (ofloxacin), Decadron® (dexamethaxone), Chloromycetin™, Voltaren®, Betoptic-S® and Pred-G®.

The dressing may include a surface adhesion promoter so as to impart tissue adhesion functionality. By way of example, the surface adhesion promoter may include a photochemical adhesion bonding (PTB) agent, e.g., rose bengal, in an amount of 0.001 to about 1 wt. %, preferably 0.1%, based on total weight of the ocular dressing. According to certain embodiments, the chitosan forming the hydrogel may be thiolated using a thiolating agent, e.g., a thioglycolic acid and/or a cysteine compound to functionalize the chitosan with a thiol group capable of forming disulfide bonds with corneal tissue.

The nanofiber mat may be comprised of nanofibers formed of a polymeric material selected from the group consisting of collagen, polyvinyl alcohols (PVA), polycaprolactones (PCL), polylactic acids (PLA) and nylons (polyamides), such as nylon-6/12 and nylon-6. The nanofibers may be of indiscriminant length and have an average diameter of between 100 nm to about 1800 nm, e.g., 175 nm to about 1275 nm.

The dressings disclosed herein may be made by electrospinning the polymeric nanofibers to form the nonwoven nanofiber mat and incorporating the chitosan hydrogel into the fiber mat. According to certain embodiments, the ocular dressings may be made by electrospinning nonwoven nanofiber mat such that the hydrogel can be deposited onto a surface thereof and then impregnated within the interstices of the mat using vacuum assistance or positive pressure assistance techniques.

These and other aspects of the present invention will become more clear after careful consideration is given to the following detailed description of a presently preferred exemplary embodiment thereof.

BRIEF DESCRIPTION OF THE DRAWINGS

Reference will be made to the accompanying drawing Figures, wherein:

FIGS. 4A and 4B are representative images of prototype nanofiber reinforced chitosan hydrogel bandages created by vacuum assistance.

DETAILED DESCRIPTION

Figure 1A:
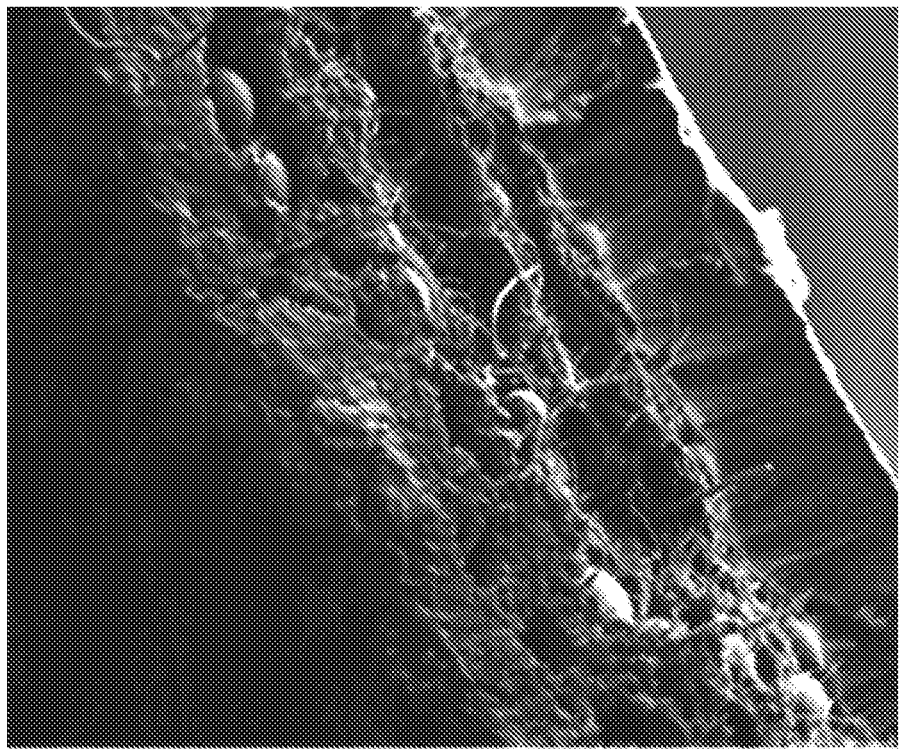
FIGS. 1A and 1B are images of a nanofiber reinforced hydrogel bandage prepared by the incorporation of a chitosan hydrogel into nylon-6 nanofiber mat to create a nanofiber-reinforced hydrogel bandages prepared by vacuum assistance and positive pressure assistance, respectively.
Figure 1B:
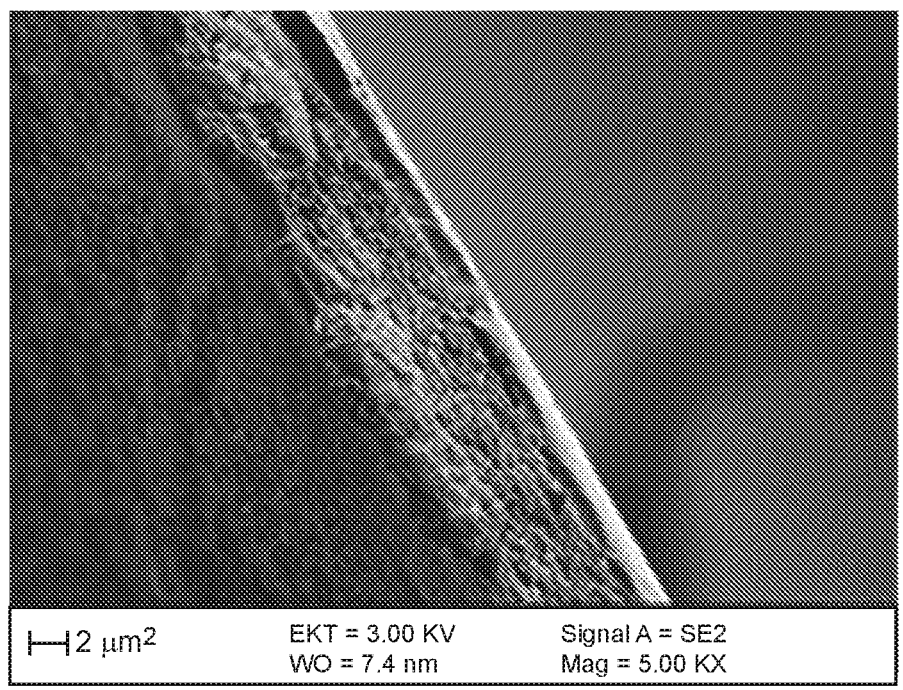

The embodiments of the invention will be further described in greater detail below.

A. Chitosan Hydrogel

The hydrogel component of the nanofiber-reinforced hydrogel matrix will necessarily include a biopolymer chitosan. Chitosan is a linear polysaccharide derived from chitin, a biopolymer found in the exoskeleton of shrimp and crabs and also produced from certain fungal sources. Chitosan is generated from chitin by the conversion of N-acetyl groups to amino groups and is soluble in dilute acid solutions. The protonated amine group lends the chitosan a polycationic nature that may promote mucoadhesion to tissue and allows for controlled interaction with negatively charged ions.

The chitosan that may be employed in the practice of the barrier materials disclosed herein can be obtained commercially from a number of sources in powdered form. The commercially obtained chitosan may also be subjected to the controlled processing conditions so as to achieve chitosan that is either water soluble or acid soluble depending upon the degree of deacetylation (DD). Thus, the chitosan may have a deacetylation degree of between about 40 to about 100%, e.g., between about 40 to 60% for water-soluble chitosan, or about 80 to about 100%, typically about 95% deacetylation for acid-soluble chitosan.

In order to obtain acid-soluble chitosan, for example, the chitosan is suspended in a 100% v/v sodium hydroxide solution that has been purged with nitrogen and heated to 120° C. for 2.5 hours. The chitosan is then filtered and rinsed until neutral, resulting in 95% deacetylated chitosan. After this deacetylation treatment, the chitosan can be easily dissolved into dilute acetic acid (0.1 Molar) at 2% w/v for incorporation into the nanofiber mat.

If water-solubility is required, then the chitosan is dissolved in 0.1 M acetic acid at 2% w/v, and acetic anhydride is then added dropwise at 0.75% v/v (based on the total solution volume) and stirred for one hour to induce reacetylation of the chitosan to 40-60% deacetylation. Upon precipitation with the addition of 3-4× volumes of acetone, the chitosan is centrifuged to remove it from solution, and the pelleted treated chitosan product is lyophilized to produce a water-soluble powder.

Deacetylation and reacetylation processing may be accomplished using high molecular weight ($M_w$=310-375 kDa), medium molecular weight ($M_w$=190-310 kDa), and low molecular weight ($M_w$=50-190 kDa) chitosan. First-derivative UV-Vis characterization may be used to quantify the degree of acetylation throughout the chitosan treatment process. It has been determined that despite the different starting degrees of acetylation, the first deacetylation treatment brings substantially all chitosan samples to a level of 95% deacetylation, after which the 0.75% v/v acetic anhydride reacetylation treatment consistently yields chitosan samples having a deacetylation level of 40-60%. Low $M_w$ chitosan may be difficult to precipitate and collect after reacetylation treatment. Medium $M_w$ and high $M_w$ chitosan are typically easier to collect. Preferably medium $M_w$ chitosan is subjected to the deacetylation-reacetylation treatment as it has been shown to form the hydrogels with the most desirable properties when dissolved at 0.5-1.5% w/v in deionized water. The chitosan hydrogel should have a molecular weight ($M_w$) between 50,000 and 375,000 g/mol.

The chitosan solvent may evaporate during processing thereby resulting in an increased brittleness of the final dressing. Hydration of the resulting bandage prior to application onto the wound site will however reduce or eliminate such brittleness was eliminated when the sample was hydrated. In order to eliminate the need for pre-application hydration, glycerol may be incorporated into the chitosan component to retain sample flexibility after the hydrogel solvent evaporates. Glycerol is a common ingredient in lubricating eye drops. It was found that glycerol addition to the chitosan hydrogel solution in an amount between about 0.5% (v/v) to about 20.0% (v/v), based on the 0.1 M Acetic Acid volume, such as between about 1% (v/v) to about 5% (v/v), e.g., about 2% (v/v) is sufficient to impart the flexibility needed for application to the ocular surface.

Following incorporation into the nanofiber mat (described in detail below), the chitosan hydrogel is preferably stabilized by the addition of an ionic crosslinker, such as sodium tripolyphosphate (NaTPP). The negatively charged oxygen atoms of NaTPP associate with the positively charged ammonium ions of the chitosan to form an ionic network that improves that physical and hydrolytic stability of the chitosan hydrogel component. The incorporation of the crosslinker can be accomplished by soaking the resulting nanofiber reinforced bandage in a solution of the crosslinker, e.g., 15% w/v NaTPP solution, for a time sufficient (e.g., about 15 seconds to about 1 minute, typically about 30 seconds, prior to rinsing in deionized water. As mentioned previously, glycerol may also be incorporated into the solutions up to 20% vol/vol, e.g., at 2% v/v, to maintain sample flexibility upon drying after the crosslinking step.

Crosslinking with 1,4-butanediol diglycidyl ether (BDDGE) can also be used to stabilize chitosan in collagen nanofiber-containing dressings, for example, through immersion of the collagen nanofiber containing dressing in a solution of BDDGE. Crosslinking can be achieved by submerging the final nanofiber reinforced chitosan dressing in a 2-5% w/v solution (pH 6.3-10.3) of BDDGE dissolved in ethanol with 2% v/v glycerol for 15 min-6 hours. By way of specific example, the collagen nanofiber reinforced chitosan dressing may be cross-linked by submersion of the dressing in a 5% BDDGE/2% glycerol solution, pH 6.3, for 6 hours to crosslink a sample 36 $cm^2$ in size.

The hydrogel solution to be incorporated into the polymeric mat thereby preferably is comprised of chitosan dissolved in 0.1 M acetic acid in deionized water (95% DD chitosan product) or pure deionized water (40-60% DD chitosan product) at concentrations between 1-3% wt/vol, e.g. 2% wt/vol. As noted previously, glycerol may be added to the hydrogel solution, e.g., in an amount of about 2% (v/v), in order to improve flexibility of the resulting cross-linked chitosan matrix.

B. Polymeric Nanofiber Mat

The biocompatible polymeric nanofibers may be formed from natural or synthetic polymeric materials. A preferred natural polymeric nanofiber is formed of collagen, e.g., Collagen Type 1. Synthetic nanofibers may be formed using conventional nanofiber fabrication techniques from a number of polymers such as, polyvinyl alcohol (PVA), polycaprolactone (PCL), polylactic acid (PLA) and nylons (polyamides), such as nylon-6/12, nylon-6 and the like.

The nanofibers may be formed by any conventional fabrication technique, e.g., electrospinning (both needle-based and needle-free), to produce a relatively dense nonwoven mat of nanofibers having the desired morphology and properties. Typically, the nanofiber mats produced by such electrospinning techniques will be in the form of a nonwoven mat containing a dense plurality of individual filaments of indeterminate length having a mean fiber diameter between about 100 nm to about 1800 nm, typically between about 175 nm to about 1275 nm. By way of example, if the nanofibers are formed of collagen (Collagen I), then the individual fibers will possess a mean fiber diameter of between about 150 nm to about 500 nm, typically between about 190 nm to about 425 nm. If a polyamide is employed, then the individual fibers will typically possess a mean fiber diameter of between about 100 nm to about 600 nm or between about 250 nm to about 550 nm. Certain specific electrospun nanofibers are noted in the Table 1 below:

TABLE 1

Mean nanofiber diameter measurements for exemplary electrospun polymers

| Polymer | Solvent System | Mean Fiber Diameter - Standard Needle-Based Electrospinning | Mean Fiber Diameter - Needle-Free Electrospinning |
|---|---|---|---|
| 16% w/v Collagen 1 | 1:1 EtOH/10X PBS | 422 ± 104 nm | — |
| 8.3% w/v Collagen 1 | HFIP | 199 ± 74 nm | 1693.2 ± 856.4 nm |
| 12% w/v Nylon-6 | 2:1 Acetic Acid:Formic Acid | 158 ± 36 nm | 128 ± 19 nm |
| 14% w/v PCL | 3:1 Formic Acid:Acetic Acid | 319 ± 74 nm | 295 ± 230 nm |
| 12.5% w/v PLLA | 1:1 DCM:DMF | 824 ± 273 nm | 253 ± 53 nm |
| 15% w/v PLLA | 3:2 DCM:DMF | 1252 ± 403 nm | — |
| 10% w/v Nylon 6/12 | HFIP | 349 ± 109 nm | 568 ± 217 nm |
| 10% w/v PVA | Water + 2.5% v/v Triton-X | 666 ± 247 nm | 396 ± 133 nm |
| 10% w/v Nylon-6 + 3% w/v PCL | 3:1 Formic:Acetic Acid | — | 187.5 ± 77.1 nm |
| 6% w/v Nylon-6 + 7% w/v PCL | 3:1 Formic:Acetic Acid | — | 218.5 ± 96.1 nm |

By way of example, PA6 nanofibers may have a mean fiber diameter of between about 100 nm to about 200 nm, e.g., between about 125 nm to about 175 nm and especially about 158 nm±36 nm when produced with standard needle-based electrospinning protocols. Needle-free electrospinning can be employed to produce nanofibers of 100 nm to about 200 nm, e.g., between about 100 nm to about 150 nm and especially about 128 nm±19 nm.

The nanofibers may be generally aligned by collecting the electrospun nanofibers on a rotating capture surface (or mandrel). By use of this technique, it is possible to align the nanofibers in a direction generally perpendicular to the mandrel's axis of rotation thereby mimicking the natural structure of the extracellular matrix. By altering the rotational speed, it is also possible to adjust the degree of alignment, allowing for the inclusion of some heterogeneity of alignment that may be necessary for the mechanical stability of the dressing in the non-aligned direction. Changing the mandrel size allows control over both the size of the resultant dressings and the surface speed of the mandrel associated with each applied voltage/RPM combination.

In general, the anisotropy of the nanofibers in the non-woven mat may vary from 0.1 to 0.5, typically about 0.2, using SEM images of the mat with an ImageJ analysis with an "OrientationJ" program whereby the anisotropy value is expressed on a scale from 0 (no alignment) to 1 (complete alignment).

Collagen nanofibers may be crosslinked using conventional techniques, such as glutaraldehyde treatment, UV-crosslinking, soaking with 1-ethyl-3-(3-dimethylaminopropyl)carbodiimide hydrochloride (EDC) or 1,4-butanediol diglycidyl ether (BDDGE) crosslinkers, and vitrification (low temperature evaporation of entrapped moisture). Preferably, collagen nanofiber crosslinking is achieved by soaking the nanofibers in a solution of 5% BDDGE in ethanol for 15 minutes.

In order to avoid glutaraldehyde crosslinking of PVA, an ethanol treatment may be used for PVA nanofibers to remove residual water within the fibers and increase the degree of crystallinity of the polymer. This results in an increase in the number of physical crosslinks within the electrospun fiber mat as intermolecular hydrogen bonding within the polymer replaces PVA-water hydrogen bonding with the increased crystallization, which has also been confirmed with an increase in hydrated prototype stability.

The resultant nanofiber mats are between 5 and 80 microns thick, typically between 5 and 50 μm, more specifically between 10 and 16 μm; The nanofiber mats will exhibit a fiber density as expressed by mat basis weight of about 1 $g/m^2$ to about 20 $g/m^2$, typically between 3 and 10 $g/m^2$, for example about 3 $g/m^2$ to about 7 $g/m^2$. Typical nanofiber mats will have a porosity of between about 35% to about 60%, e.g., between about 40% to about 50% as measured from scanning electron microscope (SEM) images.

C. Optional Components/Capabilities (i) Self-Adhesive Functionalities

Though the ocular dressings as described herein will be compatible with traditional suturing and ocular gluing methods for attachment to the ocular surface, it is widely known that sutures can cause additional trauma to already irritated tissue. Therefore, the ocular dressings as described herein may include a photoactive dye, such as rose bengal (RB) as an adhesion agent to promote adhesion to the ocular surface when activated. The photoactive dye employed in the ocular dressing may therefore be activated using conventional photochemical tissue bonding (PTB) techniques, e.g., by illuminating the dye with laser light at 532 nm.

According to certain embodiments therefore, a photoactive dye, e.g., rose bengal, may be incorporated within the chitosan hydrogel component thereby eliminating the need to separately apply the dye to the ocular surface (e.g., by surgical painting) and thereby making PTB functionality inherent to the dressing. If employed, the dye component, e.g., rose bengal, may be effectively incorporated into the chitosan hydrogel component by adding the dye component at concentrations ranging from 0.001-1 wt %, based on total weight of the ocular dressing, during the dissolution phase. The dye is then incorporated into the chitosan hydrogel component and enables photochemical tissue bonding interactions between the dressing and the corneal surface.

Alternatively, an aqueous solution of 0.001%-1 wt % based on total weight of the ocular dressing rose bengal may be applied directly onto the undyed ocular dressing prior to surgical application to the ocular trauma site.

Excitation with green laser light (532 nm) activates the rose bengal, forming bonds between amine groups and proteins in human tissue without causing an exothermic reaction. These covalent bonds serve to hold the ocular dressing in place on the corneal surface. When using amniotic membrane, bonds are formed between the collagen fibrils in the membrane and the ocular tissue due to rose bengal activation. In the synthetic biomaterial as disclosed herein, the free amine groups in the chitosan hydrogel, as well as the proteins in some of the polymeric nanofibers (collagen), will form bonds with the ocular tissue. The ability of the ocular dressing to be applied with standard suturing and gluing methods or with photochemical tissue bonding thereby provides an array of possibilities for the surgical repair of ocular trauma.

Additionally, it has been qualitatively observed that natural "tackiness" of the ocular dressing and mucoadhesive properties of chitosan can provide the ability for the dressing to adhere to the surface of an eye without the need for sutures or glue. It has therefore been found that self-adhesion capabilities of the ocular dressing to the injured corneal surface may be improved through the application of basic thiolation reactions on the chitosan hydrogel component to enable the formation of disulfide bonds with the corneal tissue upon application thereby enabling simple adhesion of the dressing over the injured surface. Thiolation of the chitosan hydrogel component may be achieved through reaction of chitosan with thioglycolic acid, glutathione, or cysteine compounds. Reaction with glutathione, thioglycolic acid or N-acetyl cysteine (in the presence of 1-ethyl-3-(3-dimethylaminopropyl)carbodiimide) enables basic functionalization of the amine group with a thiol capable of forming disulfide bonds with the corneal tissue. Adhesion to the corneal surface has been confirmed using burst-testing to demonstrate the formation of a water-tight seal and repressurization of the anterior chamber in excess of 35 mm Hg.

(ii) Therapeutic Elution

One of the key benefits provided by the conventional use of fresh amniotic membrane applied to the ocular surface is the delivery of growth factors and stem cells that promote epithelial wound healing. The ocular dressing of the embodiments disclosed herein thereby provide the potential to load therapeutics (such as antibiotics, antimicrobials, anti-inflammatories, analgesics, anesthetics, or growth factors) into the nanofiber and hydrogel components. Therapeutic agents may therefore optionally be incorporated within the fibers or the hydrogel components of the nanofiber-reinforced hydrogel dressings which thereby permit the dressings to be loaded with an effective amount of the therapeutic agent and permit its controlled delivery. Therapeutic agents include human stem cells (e.g., amniotic epithelial cells) that may be incorporated into the interstices of the nanofiber mat or within the chitosan hydrogel. Therapeutic drugs such as antibiotics (e.g., gentamycin or fluoroquinolone compounds), non-steroidal or steroidal anti-inflammatories (such as prednisolone) and mixtures thereof may be incorporated into the nanofiber mat during the electrospinning process. Specific therapeutic drugs include, by way of example, Ciloxan®, Vigamox®, Oculflox® (ofloxacin), Decadron® (dexamethaxone), Chloromycetin™, Voltaren®, Betoptic-S® and Pred-G®. Therapeutics may be incorporated into the initial polymer solution used in electrospinning in an amount of about 0.1 wt. % to about 10.0 wt/vol. %.

The therapeutic agent may alternatively or additionally be incorporated into the chitosan hydrogel. If present in the chitosan hydrogel component, therefore, the therapeutic agent may be present in an amount of about 0.01 wt. % to about 10 wt. %, based on total weight of the hydrogel and the target dosage of the specific therapeutic.

The combined use of nanofibers of varying diameter, along with selectively matching therapeutic agents with specific compatible nanofiber materials, will allow sustained release over time, negating the need to frequently reapply therapeutics in the form of eye drops. Further, the release of multiple therapeutics by simultaneously collecting different loaded nanofibers into the same nanofiber dressing can be controlled.

D. Bandage Fabrication and Properties

The resulting nanofiber reinforced chitosan hydrogel bandage or dressing will exhibit several desirable mechanical properties that are advantageous, e.g., for ocular treatment and/or repair. For example, the bandages or dressings may exhibit an elastic modulus of from about 1 MPa to about 200 MPa, typically between about 25 MPa to about 75 MPa, and a peak stress of between about 1 MPa to about 27 MPa, typically about 11 MPa to about 17 MPa. Bandages or dressings demonstrate transparencies for bandage or dressing thicknesses between about 10 to about 100 μm of from 40-95%, typically between 50% and 80%, as measured via UV-Vis at 550 nm, with a refractive index of 1.33-1.34 using an Abbe Refractometer. The bandages or dressings will also typically exhibit beneficial oxygen transmission of between about 400 to about 850 $cc/m^2$-day, e.g., between 406 to about 775 $cc/m^2$-day (ASTM F1927) and water impermeability of ≤0.1% aqueous humor transmission over 14 days.

The following exemplary processing techniques may be employed to incorporate the hydrogel into a nonwoven mat of nanofibers to form the nanofiber-reinforced hydrogel ocular dressing as disclosed herein. For all techniques disclosed, it is preferred that medium molecular weight (MMW) chitosan (Sigma, MW of 50,000 and 375,000 g/mol) is first deacetylated to at least 95% by treatment in a 100% w/v sodium hydroxide solution at 120° C. under a nitrogen purge for 2.5 hours to remove acetyl groups on the chitosan backbone, thereby rendering it more soluble. After cooling, the deacetylated chitosan solution may be rinsed with deionized water with the resulting 95% deacetylated chitosan then being filtered and washed until neutral.

To create bandages or dressings of increased thickness for improved handling and ease of application, multiple sheets of nanofiber-reinforced chitosan hydrogel dressings may be layered together. As the hydrogel component dries on a polyurethane backing, the chitosan hydrogel layers within the different nanofiber layers fuse together. The hydrogel component is then crosslinked with BDDGE, as described previously, to prevent layer delamination. Between about 1 to about 5, preferably about 2, nanofiber-reinforced hydrogel layers can be assembled and dried together.

The nanofiber-reinforced chitosan hydrogel bandages or dressings may alternatively or additionally be assembled with one or more other structural layers to provide desired functionality, e.g., additional mesh reinforcement layer(s), therapeutic layer(s) and the like.

(i) Vacuum Assistance Technique

A vacuum assistance technique may be employed to physically force the chitosan hydrogel into the interstices of the nanofiber mat, particularly with nanofiber mats composed of synthetic (non-collagen) nanofibers, so that the nanofiber mat is embedded within a matrix of chitosan. When employing this vacuum assistance technique, solutions containing between about 1% w/v to about 10% w/v chitosan in 0.1 M Acetic Acid, typically between about 2% w/v to about 5% w/v chitosan, in 2% v/v glycerol, based on total acetic acid solution volume, may be employed.

In practice, the electrospun nanofiber mats may be placed over a relative large pore (e.g., pore size of between about 74 microns to 224 microns, preferably between about 100 microns to about 200 microns, e.g., about 180 microns) mesh for support formed of a suitable material (e.g., nylon or aluminum). Pure ethanol may be distributed over the surface of the nanofiber mat for hydration. Vacuum may then be applied for a sufficient period of time (e.g., up to about 5 seconds) to pull the ethanol through the mat and hydrate the nanofiber mat. A chitosan/glycerol solution (e.g., about 4 mL of 2% w/v chitosan/1% v/v glycerol solution) may then be evenly distributed over the sample surface with vacuum then being applied until drops of chitosan solution are visible in the bottom of the filter setup (approximately 10 seconds). The resulting chitosan impregnated nanofiber mat may thereafter be dried at room temperature following which the chitosan component may be ionically crosslinked by submerging the sample in 15% w/v NaTPP/2% v/v glycerol solution for about 30 seconds and rinsing in deionized water/2% v/v glycerol. An image of a nanofiber reinforced hydrogel bandage in cross-section formed by vacuum filtration is shown in FIG. 1A.

Figure 2:
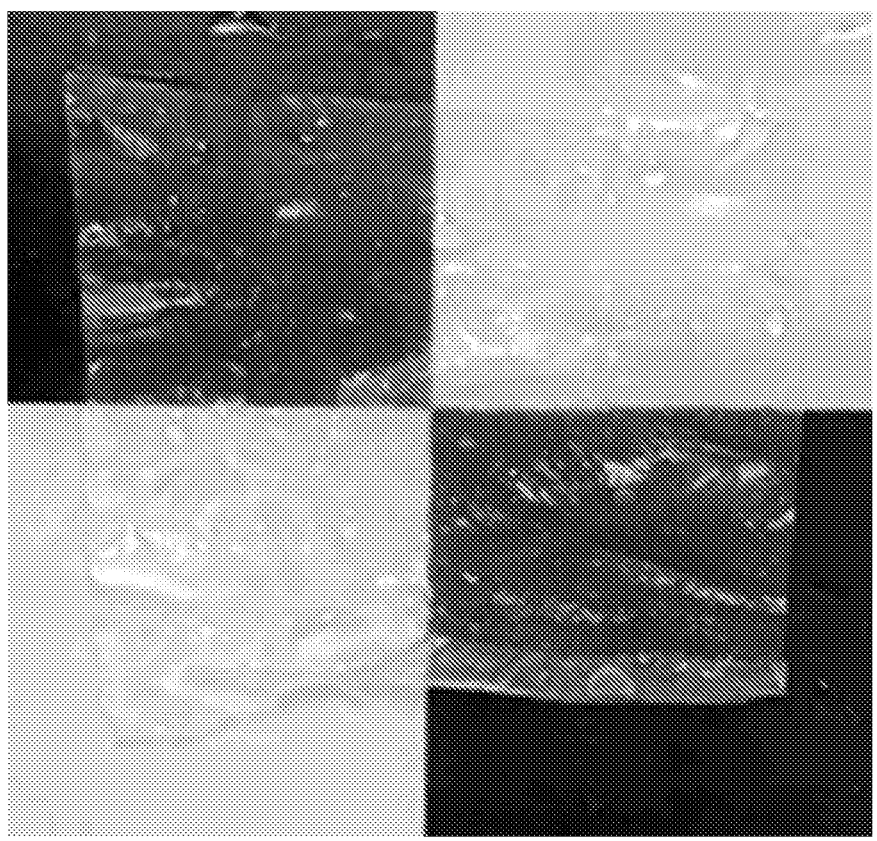
FIG. 2 is an image of a nanofiber reinforced hydrogel bandage obtained by positive pressure assistance.
Figure 3A:
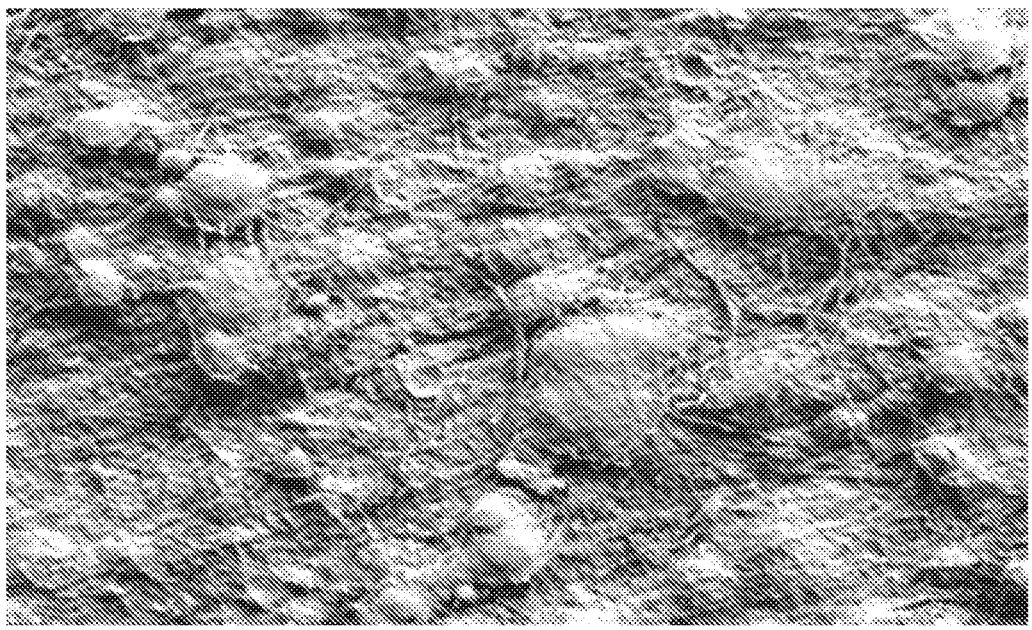
FIGS. 3A and 3B are plan and cross-sectional images, respectively, of a nanofiber reinforced hydrogel bandage obtained by vacuum assistance.
Figure 3B:
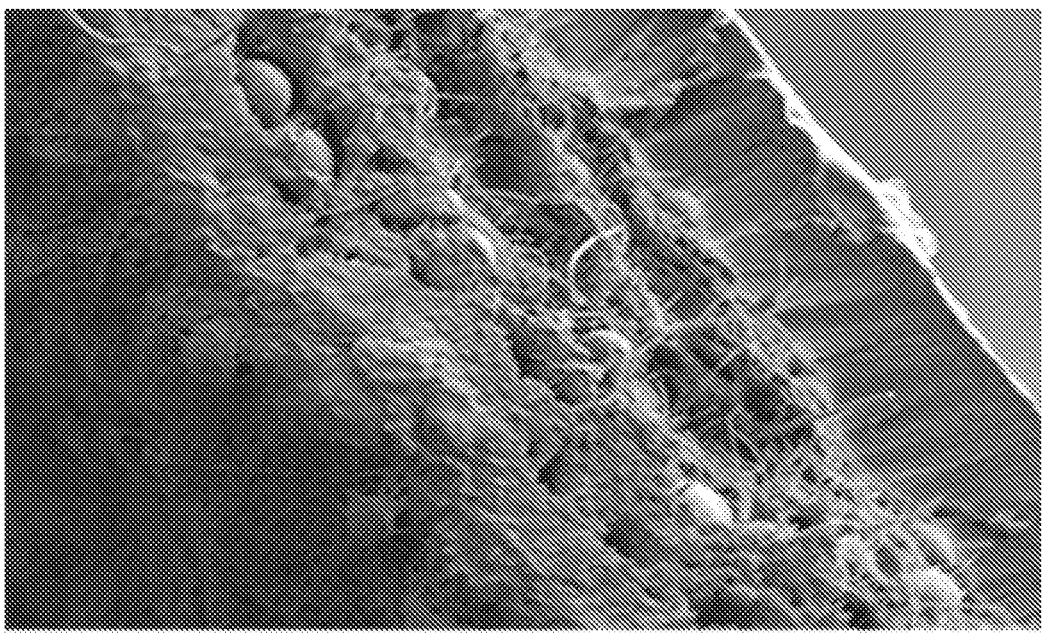

The encapsulation of the nanofiber mat in the chitosan hydrogel solution via vacuum filtration advantageously results in the dressing being transparent, pliable, and mechanically robust as shown by the image of FIG. 2. SEM analysis of vacuum cast samples depicts full permeation of the chitosan hydrogel throughout the thickness of the nanofiber mat as shown by the plan and cross-sectional views in FIGS. 3A and 3B of a nylon-6 nanofiber reinforced chitosan hydrogel bandage formed by vacuum filtration impregnation as described above. The vacuum filtration impregnation process resulted in ocular dressings that, while visually opaque when dry, became increasingly transparent with hydration.

The nanofiber reinforced chitosan hydrogel bandages according to the embodiments disclosed herein will typically have a transparency (e.g., light transmission through the bandage) of at least about 50% up to about 95% with a refractive index being between about 1.30 to about 1.45, typically about 1.34. In such a manner, therefore, the bandages in accordance with the embodiments disclosed herein enable the wound to be visibly apparent beneath the bandage so as to provide visual assistance to the medical personnel during the wound treatment. FIGS. 4A and 4B show representative images of prototype nanofiber reinforced chitosan hydrogel bandages created by vacuum filtration.

(ii) Positive Pressure Assistance Technique

The nanofiber-reinforced chitosan hydrogel bandages may also be fabricated using a positive pressure technique to incorporate the hydrogel into the interstices of the nanofiber mat component. For this production process, an electrospun nanofiber mat (approximately 9 cm×9 cm) may be placed on a suitably configured pressurization device and 10 mL of chitosan/glycerol hydrogel solution added onto the top surface of the mat. The pressure may be increased within the device using e.g., a 10 mL syringe to infuse air through the inflation port and depress the actuating plate over the nanofiber mat to thereby force the hydrogel solution to permeate into the nanofiber mat structure. Upon achieving maximal pressure within the device, a stop valve may be engaged to enable the chitosan impregnated nanofiber mat to remain within a pressurized environment for up to 15 minutes. The resultant bandage construct was removed from the system and left to dry at room temperature on a polyurethane backing.

The pressurization time is selected so as to ensure sufficient hydrogel incorporation in the nanofiber mat. In this regard, a pressurization time of between about 5 to about 20 minutes, typically about 15 minutes, is usually sufficient to ensure adequate hydrogel incorporation into the nanofiber mat. Pressures of between about 10 psi to about 50 psi, e.g., between about 30 psi to about 50 psi (typically about 45 psi), may be employed for this technique.

EXAMPLES

Prototype dressings were produced via the positive pressure technique described previously. Specifically 6 cm×6 cm sections of electrospun nylon-6 nanofiber mats were submerged in 20 mL ethanol for 30 seconds and laid flat across the bottom of the positive pressure system chamber. 20 mL of 2% w/v chitosan and 2% v/v glycerol in 0.1 M acetic acid were pipetted on top of the nanofiber mat. The system is pressurized to 45 psi for 15 minutes to infuse the chitosan solution into the nanofiber mat. Following chitosan solution infusion, the bandages were removed and dried under ambient conditions for 24 hours as single or double layered constructs.

Tables 2A and 2B 1 below summarize the cumulative average dressing thickness and the nanofiber:hydrogel mass ratio of nylon-6 nanofiber reinforced samples produced via the positive pressure system. The chitosan component of the dressing was subsequently stabilized via crosslinking in 1,4-butanediol diglycidyl ether (BDDGE; 5% w/v in ethanol+2% v/v glycerol) for 6 hours. Table 2 below summarize the cumulative average dressing thickness and nanofiber:hydrogel mass ratio of samples after crosslinking.

TABLE 2A

Positive Pressure Technique Dressing Production

| Sample Description | Dressing Thickness (μm) | Nanofiber:Hydrogel Mass Ratio |
|---|---|---|
| CS-DA Hydrogel | | |
| Nylon-6, Single Layered (n = 113) | 25.3 ± 6.5 | 0.26 ± 0.10:1 |
| Nylon-6, Double Layered (n = 64) | 47.3 ± 14.2 | 0.29 ± 0.10:1 |
| CS-NAC 15% Hydrogel | | |
| Nylon-6, Single Layered (n = 13) | 28.3 ± 6.9 | 0.20 ± 0.10:1 |
| Nylon-6, Double Layered (n = 10) | 48.7 ± 7.8 | 0.27 ± 0.06:1 |
| CS-NAC 30% Hydrogel | | |
| Nylon-6, Single Layered (n = 28) | 30.6 ± 6.8 | 0.30 ± 0.16:1 |
| Nylon-6, Double Layered (n = 17) | 47.5 ± 7.5 | 0.35 ± 0.14:1 |
| CS-NAC 40% Hydrogel | | |
| Nylon-6, Single Layered (n = 15) | 21.8 ± 3.9 | 0.33 ± 0.13:1 |
| Nylon-6, Double Layered (n = 13) | 44.7 ± 8.8 | 0.40 ± 0.06:1 |
| CS-NAC 80% Hydrogel | | |
| Nylon-6, Single Layered (n = 1) | 21.9 | 0.18:1 |
| Nylon-6, Double Layered (n = 4) | 35.6 ± 6.9 | 0.40 ± 0.15:1 |

TABLE 1B

Dressing Production Post-Crosslinking

| Sample Description | Dressing Thickness (μm) | Nanofiber:Hydrogel Mass Ratio |
|---|---|---|
| CS-DA Hydrogel | | |
| Nylon-6, Single Layered (n = 46) | 25.0 ± 6.3 | 0.38 ± 0.11:1 |
| Nylon-6, Double Layered (n = 42) | 44.4 ± 11.8 | 0.48 ± 0.14:1 |

TABLE 1B-continued

Dressing Production Post-Crosslinking

| Sample Description | Dressing Thickness (μm) | Nanofiber:Hydrogel Mass Ratio |
|---|---|---|
| CS-NAC 15% Hydrogel | | |
| Nylon-6, Single Layered (n = 9) | 19.6 ± 4.0 | 0.55 ± 0.23:1 |
| Nylon-6, Double Layered (n = 7) | 42.5 ± 5.6 | 0.59 ± 0.15:1 |
| CS-NAC 30% Hydrogel | | |
| Nylon-6, Single Layered (n = 18) | 18.8 ± 1.9 | 0.44 ± 0.09:1 |
| Nylon-6, Double Layered (n = 16) | 38.8 ± 9.0 | 0.83 ± 0.38:1 |
| CS-NAC 40% Hydrogel | | |
| Nylon-6, Single Layered (n = 15) | 18.1 ± 4.2 | 0.70 ± 0.30:1 |
| Nylon-6, Double Layered (n = 13) | 35.8 ± 6.4 | 0.15 ± 0.15:1 |
| CS-NAC 80% Hydrogel | | |
| Nylon-6, Single Layered (n = 1) | 17.2 | 0.31 |
| Nylon-6, Double Layered (n = 4) | 28.2 ± 0.42 | 0.94 ± 0.41:1 |

The hydrogel component for samples above labeled CS-NAC was thiolated as described above using N-acetyl cysteine Table 3 below summarizes the final properties of a standard non-thiolated nanofiber reinforced ocular dressing and thiolated embodiments thereof.

TABLE 3

Functional properties of dressing prototypes

| | Standard Dressing | Thiolated Dressing |
|---|---|---|
| Thickness | 44.4 μm | 28.2-42.5 μm |
| Refractive Index | 1.33-1.34 | TBD |
| Transparency | 69.6%-81% | 45.9%-50.9% |
| Tensile Strength | 11.9 MPa | 11.3-16.7 MPa |
| Toughness | 0.94 MPa | 2.7-3.9 MPa |
| Tensile Strain | 14.5% | 39.2-40.1 MPa |
| Elastic Modulus | 77.4 MPa | 23.1-24.8 MPa |
| O2 Transmission | 1935 cc/m$^2$ day | 3691 cc/m$^2$ day |
| Water Permeability | 0.010-0.011% | (not tested) |
| Cytocompatibility | similar to controls | similar to controls |
| Shelf-Life | ≥3 months | (not tested) |

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A sutureless ocular medical dressing comprising:
a thiolated chitosan hydrogel matrix which comprises a deacetylated chitosan having a degree of deacetylation (DD) of between 40 to 100%, and
a non-woven polymeric nanofiber mat embedded in the thiolated chitosan hydrogel matrix, wherein
the thiolated chitosan hydrogel is thiolated with a thiolation agent selected from the group consisting of thioglycolic acids, glutathiones and cysteine compounds so as to be functionalized with a thiol group configured to form disulfide bonds with corneal tissue and thereby adhere the ocular medical dressing to the corneal tissue without sutures.

2. The sutureless ocular medical dressing according to claim 1, which further comprises a surface adhesion promoter and/or a therapeutic agent.

3. The sutureless ocular medical dressing according to claim 2, wherein the therapeutic agent comprises human stem cells or a therapeutic drug.

4. The sutureless ocular medical dressing according to claim 3, wherein the therapeutic drug is selected from the group consisting of gabapentin, venlafaxine, fentanyl and lidocaine.

5. The sutureless ocular medical dressing according to claim 2, wherein the surface adhesion promoter comprises a photochemical adhesion bonding (PTB) agent.

6. The sutureless ocular medical dressing according to claim 5, wherein the PTB agent is rose Bengal in an amount of 0.001 to about 0.1 wt. %, based on total weight of the ocular dressing.

7. A method of forming the sutureless ocular medical dressing according to claim 1, comprising the steps of:
(a) electrospinning nanofibers to form the nonwoven polymeric non-woven polymeric nanofiber mat; and
(b) incorporating the thiolated chitosan hydrogel into the non-woven polymeric nanofiber mat.

8. The method according to claim 7, wherein step (b) is practiced by incorporating the thiolated chitosan hydrogel into interstices of the non-woven polymeric nanofiber mat by vacuum or positive pressure assistance.

9. The method according to claim 8, wherein step (b) is practiced by applying the thiolated chitosan hydrogel onto a surface of the non-woven polymeric nanofiber mat and thereafter subjecting the non-woven polymeric nanofiber mat to vacuum or positive pressure conditions to cause the thiolated chitosan hydrogel to be impregnated within interstices of the non-woven polymeric nanofiber mat.

10. The sutureless ocular medical dressing according to claim 1, wherein the deacetylated chitosan has a molecular weight (Mw) between 50,000 and 375,000 g/mol.

11. The sutureless ocular medical dressing according to claim 10, wherein the thiolated chitosan hydrogel comprises glycerol as a plasticizing agent in an amount up to 5% v/v.

12. The sutureless ocular medical dressing according to claim 1, wherein the non-woven polymeric nanofiber mat comprises nanofibers formed of a polymeric material selected from the group consisting of collagen, polyvinyl alcohols (PVA), polycaprolactones (PCL), polylactic acids (PLA) and polyamides (PA).

13. The sutureless ocular medical dressing according to claim 12, wherein the polymeric material is polyamide-6/12 or polyamide-6.

14. The sutureless ocular medical dressing according to claim 1, wherein the non-woven polymeric nanofiber mat comprises nanofibers having an average diameter of between 100 nm to about 1800 nm.

15. The sutureless ocular medical dressing according to claim 14, wherein the average diameter of the nanofibers is between about 175 nm to about 1275 nm.

16. A multilayer bandage, wherein the bandage comprises at least one layer comprising the sutureless ocular medical dressing according to claim 1.

17. The multilayer bandage according to claim 16, wherein the bandage comprises at least one other layer which comprises a structural layer.

18. The sutureless ocular medical dressing according to claim 1, wherein the thiolated chitosan hydrogel is thiolated with N-acetyl cysteine.

19. The sutureless ocular medical dressing according to claim 1, wherein the nanofibers are formed of nylon-6 and have an average diameter of the nanofibers is between about 100 nm to about 200 nm.

20. The sutureless ocular medical dressing according to claim 1, wherein the dressing is a surgical dressing for treatment and/or repair of ocular injuries.

21. The sutureless ocular medical dressing according to claim 1, wherein the non-woven polymeric nanofiber mat has a thickness between about 5 and 80 microns.

22. The sutureless ocular medical dressing according to claim 1, wherein the non-woven polymeric nanofiber mat has a basis weight of between about 1 $g/m^2$ to about 20 $g/m^2$.

23. The sutureless ocular medical dressing according to claim 1, wherein the non-woven polymeric nanofiber mat has a porosity of between about 35% to about 60% as measured by scanning electron microscope (SEM) images.

24. The sutureless ocular medical dressing according to claim 1, wherein the sutureless ocular medical dressing has an elastic modulus of from about 1 MPa to about 200 MPa.

25. The sutureless ocular medical dressing according to claim 1, wherein the sutureless ocular medical dressing has a peak stress of between about 1 MPa to about 27 MPa.

26. The sutureless ocular medical dressing according to claim 1, wherein the sutureless ocular medical dressing exhibits transparency to 550 nm light of from about 40 to about 95% at dressing thickness of between 10 to 100 μm and a refractive index (RI) of between about 1.33 to about 1.34.

27. The sutureless ocular medical dressing according to claim 1, wherein the sutureless ocular medical dressing exhibits an oxygen transmission according to ASTM F1927 of between about 400 to about 850 $cc/m^2$-day.

28. The sutureless ocular medical dressing according to claim 1, wherein the sutureless ocular medical dressing exhibits water permeability of ≤0.1% aqueous humor transmission over 14 days.

29. The sutureless ocular medical dressing according to claim 1, wherein the thiolated chitosan hydrogel is present in a mass ratio of nanofibers of the non-woven polymeric nanofiber mat to the thiolated chitosan hydrogel of between 0.01:1 to 10:1.

\* \* \* \* \*